United States Patent [19]

Farwell

[11] Patent Number: 4,941,477
[45] Date of Patent: Jul. 17, 1990

[54] METHOD AND APPARATUS FOR DETECTION OF DECEPTION

[75] Inventor: Lawrence A. Farwell, Urbana, Ill.

[73] Assignee: University Patents, Inc., Westport, Conn.

[21] Appl. No.: 279,585

[22] Filed: Dec. 2, 1988

Related U.S. Application Data

[63] Continuation of Ser. No. 94,956, Sep. 9, 1987, abandoned.

[51] Int. Cl.$^5$ .................................................. A61B 5/04
[52] U.S. Cl. .................................................... 128/731
[58] Field of Search ............................... 128/731–732, 128/905

[56] References Cited

U.S. PATENT DOCUMENTS

| | | | | |
|---|---|---|---|---|
| 3,780,724 | 12/1973 | John | ..................................... | 128/731 |
| 4,216,781 | 8/1980 | John | ..................................... | 128/731 |
| 4,244,376 | 10/1981 | Fisher et al. | ........................ | 128/731 |
| 4,699,153 | 10/1987 | Shevrin et al. | ...................... | 128/731 |

OTHER PUBLICATIONS

Siarkiewicz, Piotr H. et al., Europ. Pat. Appln. Publ. No. EP0151656, published 21.08.85.

Primary Examiner—Francis Jaworski
Attorney, Agent, or Firm—George M. Yahwak

[57] ABSTRACT

A method and apparatus for detecting concealment of hidden information in interrogative polygraphy is described which employs Event Related Brain Potentials (ERP). Various stimuli are presented to a subject and the P300 components of the subject's ERP's are monitored and analyzed. Three types of stimuli are presented, Probe which are relevant to the "crime", Irrelevant—having no bearing on the crime, and Target which require the subject to perform an act. If, and only if, the subject has guilty knowledge, the Probe stimuli, like the Target stimuli, elicit a large ERP and provide a guilty indication.

16 Claims, 4 Drawing Sheets

| Stimulus Type | Relative Frequency | Description | Instructions | Stimulus Evaluation | Predicted ERP |
|---|---|---|---|---|---|
| Target | 1/6 | Not Crime Relevant | Count Silently | Rare, Task Relevant | P300 |
| Irrelevant | 2/3 | Not Crime Relevant | No Action Required | Frequent, Irrelevant | No P300 |
| Probe | 1/6 | Crime Relevant | No Action Required | If Innocent: Frequent, Irrelevant (Indistinguishable from Irrel.) | No P300 |
| | | | | If Guilty: Rare, Noteworthy | P300 |

FIG. 7

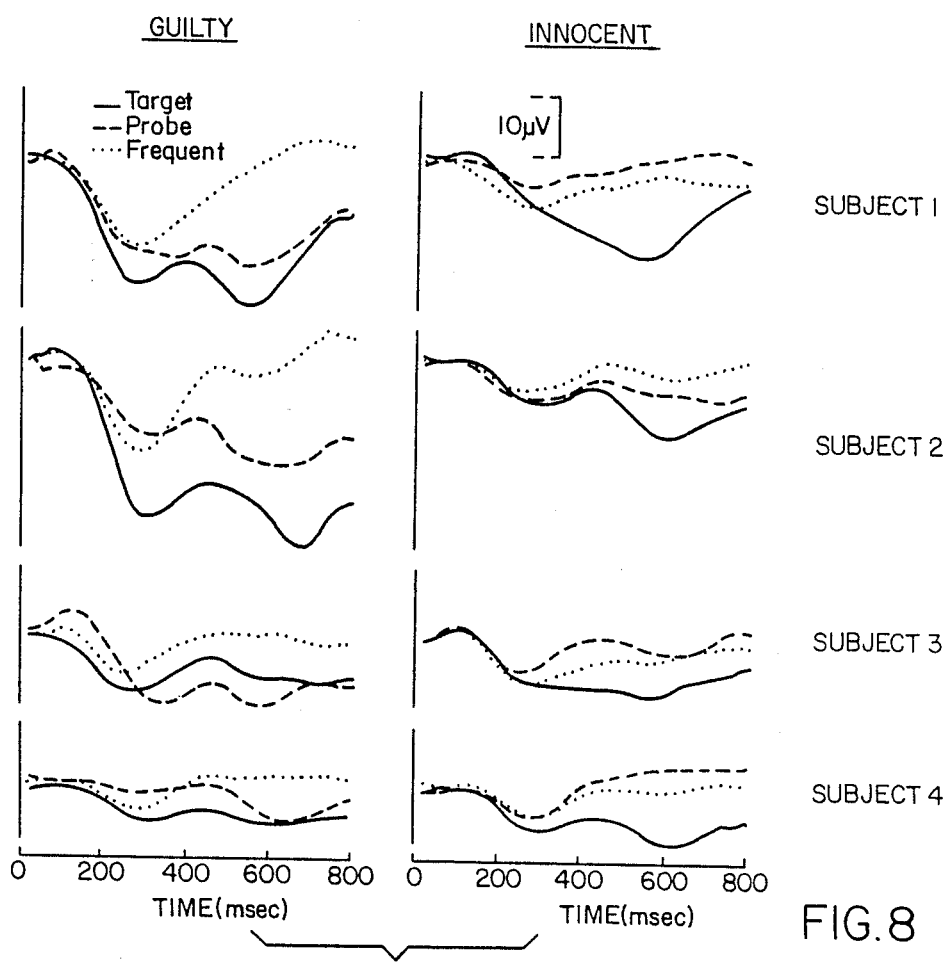

FIG. 8

METHOD AND APPARATUS FOR DETECTION OF DECEPTION

This is a continuation of application Ser. No. 94,956, filed 9/9/87, and now abandoned.

Funding which led to the making of the invention described herein may be interpreted as coming within the purview of research conducted "in the performance of work under" a federal grant. Accordingly, the United States government may have certain statutory rights to the invention described herein under chapter 38 of Title 37 USC.

FIELD OF THE INVENTION

This invention relates to methods and means for the detection of deception or Interrogative Polygraphy (IP) and more particularly to the use of electroencephalography (EEG) in Interrogative Polygraphy.

BACKGROUND OF THE INVENTION

Conventional IP techniques consist of asking questions of a subject and recording verbal and physiological responses. Psychophysiological measurements employed in the detection of deception have typically included skin conductance or skin resistance, continuously monitored blood pressure (and, since each heartbeat results in changes in blood pressure, heart rate), and breathing as measured by expansion of the chest. No psychophysiological measure has ever been found to actually measure deception. Rather, certain physiological response patterns have been held to be indicative of particular emotional responses that are likely to accompany deception in a well-orchestrated interrogation situation.

The questions asked of the subject in conventional IP techniques fall into four categories: Relevant questions, Irrelevant questions, Control questions, and Concealed Information questions. Relevant questions are questions directly related to the focus of an investigation. Irrelevant questions are irrelevant to the investigation and are structured so as to have little or no emotional significance for the subject. They are used for the purpose of comparison. Responses to these questions establish the typical response of the subject to questions about which he is not concerned.

Control questions are questions that are not directly relevant to the situation under investigation, but are designed to elicit an emotional response from the subject that is similar to the response elicited by the Relevant questions from a guilty subject. They are often general questions about types of undesirable behavior in which the subject may have been involved in the past, and are designed to elicit concern and/or doubt in the subject about the veracity of his response, or perhaps to stimulate the subject to lie. They, too, are used for the purpose of comparison: they establish the typical physiological response of a subject to questions about which the subject is concerned.

Concealed Information questions focus on information about the crime or situation under investigation that would be known only to the guilty party. It is hypothesized that a guilty individual will respond more to (that is, be more physiologically aroused by) correct details about the crime than to incorrect details, but that innocent subjects will respond the same to either.

These four types of questions are employed in three different techniques of questioning, the Relevant/Irrelevant (R/I) technique, the Control Question technique (CQT), and the Concealed Information technique.

The original "lie detection" technique was the Relevant/Irrelevant technique. In the R/I technique, two types of questions are presented: Relevant and Irrelevant. It is presumed that an innocent person will respond the same to the two types of questions because the person is unconcerned about the crime, whereas a guilty person will be more aroused by the Relevant questions, because the person is more concerned about the crime.

This technique has some serious drawbacks, the most obvious of which is that the Relevant questions concern subject matter that is inherently more upsetting than the Irrelevant questions. Therefore a large response to the Relevant questions may be the result of the emotional tendencies and physiological lability of the subject, rather than of deception. Moreover, in the cases where the subject does not respond at all to the Relevant questions, there is no indication that the subject would have responded had the questions been about the subject's criminal activity. In short, there is no control, and as a result both false negatives and false positives occur. Because of this, the R/I technique is seldom used in investigations of a specific crime or situation, although it is still used in nonspecific investigations such as preemployment and personnel screening.

The most frequently employed technique in the investigation of specific crimes or situations is the Control Question Technique, which was developed to deal with some of the problems of the R/I technique. In the CQT, subjects are asked not only Relevant and Irrelevant questions, but also Control questions designed to elicit an emotional response. It is hypothesized that an innocent subject will respond more to the Control questions, since the subject is not concerned about the crime at hand, whereas a guilty person will respond more to the Relevant questions, since the person is more concerned with the crime than with a general question about something undesirable he may have done in the past.

Concealed information techniques are of two kinds: the Guilty Knowledge test and the Peak of Tension test. Both work on the premise that a guilty person will exhibit a larger physiological response to correct details about the crime under investigation than to similar details that do not fit the crime, whereas an innocent person will respond the same to both.

In the Guilty Knowledge test, subjects are asked a variety of questions about details of the crime that would be known only to the guilty party. Unlike the other techniques mentioned, this test can employ multiple-choice questions as well as "yes or no" questions. It is hypothesized that a guilty person will respond differentially to the correct, crime-relevant details.

In the Peak of Tension test, a question concerning a relevant and correct detail about a crime is embedded in a series of parallel questions mentioning similar but incorrect details. The sequence of questions is known in advance to the subject. It is hypothesized that the physiological response will peak at the time of the relevant question.

While the aforementioned tests are presumed to measure physical responses to provocative/innocent questions, it is known that such tests are subject to countermeasures by a determined, knowledgeable and trained subject. Moreover, it is known that the stimuli for all of the physical responses measured by the detection apparatus arise in the brain. While the art of measuring electrical signals emanating from the brain (scalp) is well developed, no effort, to the inventors' knowledge, has been made to use those measurements in IP, to discover whether subjects have or do not have concealed information or information regarding the subject of an investigation.

It is known that information obtained by recording Event-Related Brain Potentials (ERP's) can be used as a tool in the study of cognitive functions. These psychophysiological data augment the data that can be obtained by the traditional methods of psychology, which rely on the measurements of overt performance or on subjective reports. Such data are obtained by placing electrodes on a person's head and recording electroencephalograph (EEG) activity while the person is engaged in a task. Using the technique of signal averaging, information can be extracted from the EEG in the form of an ERP that is time-locked to some event of interest. One component of the human ERP is the P300 signal which was first reported by Sutton et al. "Evoked-Potential Correlates of Stimulus Uncertainty" *Science*, 1965, 150, 1187-1188.

Since this initial report, the P300 has been observed in a wide variety of difference circumstances. This invention makes use of the P300, a positive-going component of the ERP with a modal latency of about 300 msec. (time measured from stimulus to peak of the P300 component). An extensive body of research has shown that the P300 component of the ERP can be used to distinguish reliably between stimuli that are comparatively infrequent (rare) and/or contain meaningful information for an individual, as compared to stimuli that are comparatively more frequent and/or do not contain relevant information. The paradigm used for this purpose is known as the "Oddball" paradigm. In this paradigm a Bernoulli series of events is presented to the subject (i.e. on any given trial, one of two stimuli can occur, and their probability is complementary). If attention is paid to the entire series and one (or perhaps two) of the classes of events or stimuli in the sequence (the "oddballs") appear with a lower probability, then events in the rare class or classes will elicit a larger P300. If these comparatively rare stimuli contain information that is relevant, meaningful, or noteworthy for the subject, then the P300 component elicited by these stimuli will be larger still.

The P300 response occurs as soon as the subject has recognized and categorized the stimulus, after only about 300 milliseconds. There is no evidence in the published literature that the P300 component can be suppressed as long as the subject recognizes the stimuli and knows to which category it belongs. Behavioral manipulations of the type used as counter-measures in conventional detection of deception methods (e.g. tightening muscles to elevate blood pressure) can begin only after stimuli have been recognized and categorized—and the resulting P300 elicited. These P300's can be detected with excellent reliability by using readily available EEG equipment.

It is an object of the present invention to utilize a subject's EEG signals in IP.

It is a further object of this invention to provide an IP system based upon monitoring and processing of a subject's P300 components.

It is a further object of this invention to provide an EEG based interrogative polygraphy system which manifests high accuracy.

SUMMARY OF THE INVENTION

This invention provides a method and apparatus for IP using electrophysiological recordings of brain activity. In this the method is distinct from the methods of IP which capitalize on measures of bodily activity that reflect changes in the subject's emotions. The electrophysiological measures used are Event Related Brain Potentials (ERP's) elicited by words, or images. The ERP's can be used to determine if the subject possesses information that can only be available to persons who were involved in a crime or in a situation that is the subject of the interrogation. The technique determines whether a P300 component of an ERP is elicited by a class of stimuli which have special meaning for a person if, and only if, that person has the specialized knowledge which is the target of the investigation.

The stimuli which carry this specialized meaning are called "probes". The person interrogated (the "subject") is presented with a series of stimuli. Most stimuli, say 80% of the series, are "Irrelevant" in the sense that they carry no special meaning for the subject. The Irrelevant stimuli are mixed in with a relatively small number of "Targets". The subject is given a list of the Target stimuli and instructed to count or do some other act with respect to them. Thus, the Target stimuli are both rare and relevant for the subject and, therefore, they are all expected to elicit a P300. An important feature of the invention is in the use of the "probes" which for an "innocent" subject are indistinguishable from the "Irrelevant" stimuli and, therefore, will not elicit a P300. However, for the "guilty" subject, the probes are distinct and constitute a group of noticeable, rare events that will elicit a P300.

In other words, for the "innocent" the series consists of a 2 category "oddball" paradigm in which the targets elicit a P300 and both probes and Irrelevant stimuli fail to elicit a P300. For the "witting", the series constitutes a 3 category "oddball" in which the targets and the probes elicit a distinct P300 while the Irrelevants do not elicit the response. The invention's signal-detection algorithm provides a precisely defined determination of whether or not the probes elicited a P300 and a statistical confidence level for this determination.

DESCRIPTION OF THE DRAWINGS

FIG. 7 is a chart which defines the various stimuli employed with this invention and the expected responses.

FIG. 8 is a plot of average P300 responses at the Pz electrode site from four subjects in response to various stimuli.

DESCRIPTION OF THE PREFERRED EMBODIMENT

Figure 1:
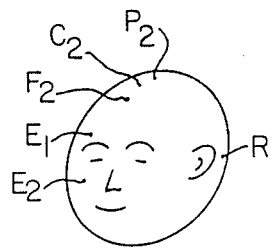
FIG. 1 is a schematic indicating the placement of certain EEG electrodes on a subject's head.

In this invention, a subject who denies knowledge of the details of a crime, or other situation under investigation, is presented with stimuli of three distinct varieties. In the preferred embodiment, the stimuli are presented as either words or pictures by a computer controlled display (CRT). However, any other mode of presentation, whether oral or pictorial, is contemplated. Event related brain potentials (ERP's) are extracted from the EEG which is recorded from EEG electrodes placed on the subject's scalp. In contrast to conventional IP, ("lie detection"), the stimuli eliciting these ERP's need not be questions to which the subject must respond verbally. In deed, the procedure described here does not require any particular verbal or externally observable response from the subject.

The stimuli are of three types: Probe, Target and Irrelevant. Probe stimuli are correct details pertinent to the situation being investigated. They can be words describing a particular detail of the scene of the crime, the events, people involved, or other details known only to a guilty or involved party. Alternatively, they can be pictures of the scene of the crime, or of people, or distinctive objects involved. Probe stimuli constitute a relatively small proportion of the stimuli presented and are denoted as "rare" stimuli. (approximately 1/6th of the stimuli).

Irrelevant stimuli are stimuli that are similar to the Probe stimuli but do not contain correct information about the crime or situation under investigation. For example, Irrelevant stimuli can include pictures of strangers or incorrect details about the crime. Irrelevant stimuli constitute the majority (approximately ⅔) of the stimuli presented to the subject.

Target stimuli are similar to the Irrelevant stimuli in content. However, the subject is given a list of the Target stimuli and instructed to respond to Target stimuli in a specific manner. The subject may be given a list of the Target stimuli and instructed to count them when they appear or, optionally, to push a button each time a certain number of Target stimuli have been counted. Like Probe stimuli, Target stimuli are relatively rare, appearing about one out of every six stimuli.

For an innocent individual, the Probe and Irrelevant stimuli are indistinguishable in content. Thus, for the innocent subject there are two recognizable groups of stimuli: (1) Target stimuli which are relatively rare, but which are recognized as different because the subject has been instructed to do something when they appear (e.g. count them) and (2) Probe and/or Irrelevant stimuli which are indistinguishable since the subject lacks knowledge about the details of the crime. For a guilty subject however, there are three recognizable groups of stimuli: (1) Target stimuli which require the subject to perform some act in response; (2) Probe stimuli (relatively rare) which the guilty person recognizes as different from Irrelevant because of familiarity with the crime and (3) Irrelevant stimuli which appear frequently.

As aforestated, research on the P300 component of the ERP has shown that when a sequence of stimuli is presented to a subject, a comparatively larger P300 component is elicited by stimuli that are characterized in a "rare category" as compared with stimuli that are categorized in a "frequent" category. The rare/frequent experimental paradigm is known as the "oddball" paradigm because the rare stimuli are "oddballs" embedded in a sequence of more frequently appearing stimuli. Prior research has shown that if the rare or "oddball" stimuli are task-relevant or noteworthy to the subject, the P300 is somewhat enhanced. This invention makes use of this prior knowledge by using the P300 component to determine the existence of information being concealed by a subject. In essence, the invention creates a two-category oddball series for an innocent person, and a 3-category oddball series for a guilty person. It is important to note that the differentiation is imposed on the same series of stimuli by the knowledge in the subject's possession. For an innocent person, only one category of stimuli, the Targets, are rare. Also, only the Targets are noteworthy—because they are being counted or otherwise noted. For a guilty person, there is an additional set of rare stimuli (i.e. the Probes). Only a guilty person knows that they constitute a separate category, i.e. that of stimuli that present correct details of the particular situation being investigated. Moreover, the Probe stimuli are noteworthy to the guilty subject because they are relevant to a crime that the subject has committed. Thus, innocent individuals exhibit P300 components in response to the Target stimuli and do not differ in their responses to the Probes and the Irrelevant stimuli. Guilty individuals exhibit P300 components to both the Target and Probe stimuli. All subjects exhibit responses lacking a P300 component to the Irrelevant stimuli.

Turning now to FIG. 1, the EEG electrode positions are shown. The positions labeled Fz, Cz and Pz refer to the frontal, central and parietal sites defined in the 10–20 International EEG Placement Standard. Reference electrodes are attached at points R on the mastoid immediately beneath and behind the subject's ears. One such electrode is placed behind each ear, and they are tied together to provide a reference. Electrodes E1 and E2 are placed immediately above and below the right eye for the purpose of recording eye movement artifact which is then utilized to exclude trials during which blinking or other substantial eye movement artifacts occur.

Figure 2:
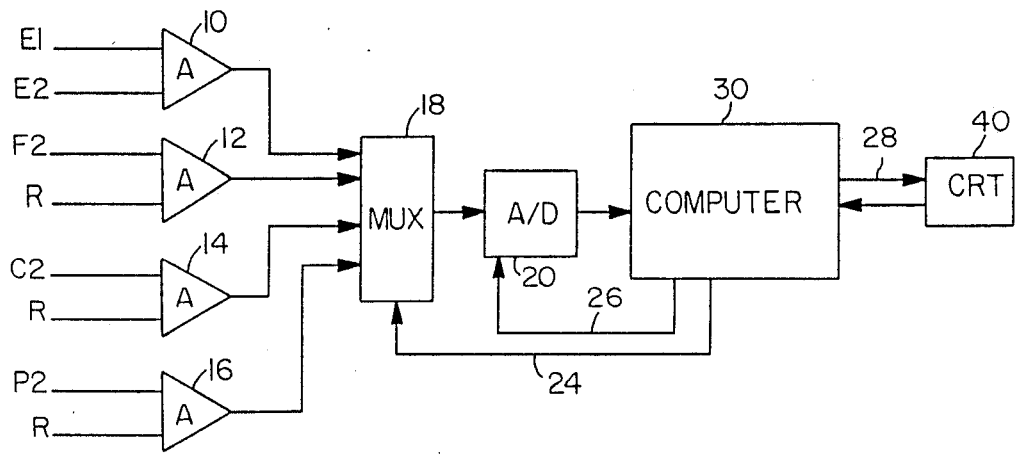
FIG. 2 is a schematic block diagram of the invention.

Turning now to FIG. 2, a block diagram is shown of the circuit components used to detect and analyze the P300 components and other artifacts sensed by the EEG electrodes. Each of amplifiers 10, 12, 14 and 16 are of the differential type which provide an output proportional to the difference in signals on their inputs. The "Model 12" amplifier produced by the Grass Instruments Co., 101 Old Colony Avenue, Quincy, Mass. 02169 is suitable for this purpose. The outputs of each of differential amplifiers 10, 12, 14 and 16 are sampled by multiplexer 18; digitized by A to D converter 20; and the digital representation is in turn fed to computer 30. Also connected to computer 30 is a CRT display terminal 40 which may be used to present stimuli to the subject under interrogation.

The inputs to each of differential amplifiers 10, 12, 14 and 16 are derived from contacts positioned at the sites shown in FIG. 1 and provide inputs to computer 30 of signals which are indicative of the P300 components sensed at the Fz, Cz and Pz EEG positions as well as the eye electrode signals. The outputs of differential amplifiers 10, 12, 14, and 16 are serially multiplexed by multiplexer 18 and subsequently digitized in A to D converter 20. CRT 40 is instructed (via conductor 28) to provide the required stimulus to the subject.

Computer 30 controls the rate of signal sampling by multiplexer 18 via conductor 24. In addition, computer 30 instructs A/D converter 20 to digitally convert the analogue samples to digital representations. In this way, computer 30 receives digital samples from A/D converter 20 on a regular basis (e.g. a sample every 20 milliseconds from each differential amplifier). The sampling takes place, preferably, for 800 milliseconds following stimulus presentation to the subject. This time is defined as the "trial time". It should be understood that the sampling times and duration of sample can be altered to fit the desired circumstances.

Figure 3:
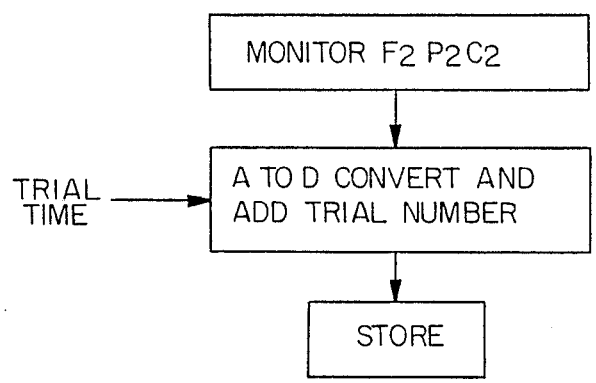
FIG. 3 is a simplified flowchart of a portion of the program carried out by the circuit of FIG. 2.

As shown in the brief flowchart of FIG. 3, each of the EEG positions Fz, Cz and Pz are continuously monitored and are sampled at a trial time; the sensed waveforms are converted to a series of digital numbers and a trial number added to identify the origin of the digitized waveforms; and the data then stored for subsequent processing. As the various EEG signals are sensed etc., the eye movement artifacts are also sensed and compared to a predetermined level. If the artifact is too large, the trial during which the artifact occurs is discarded.

Figure 4:
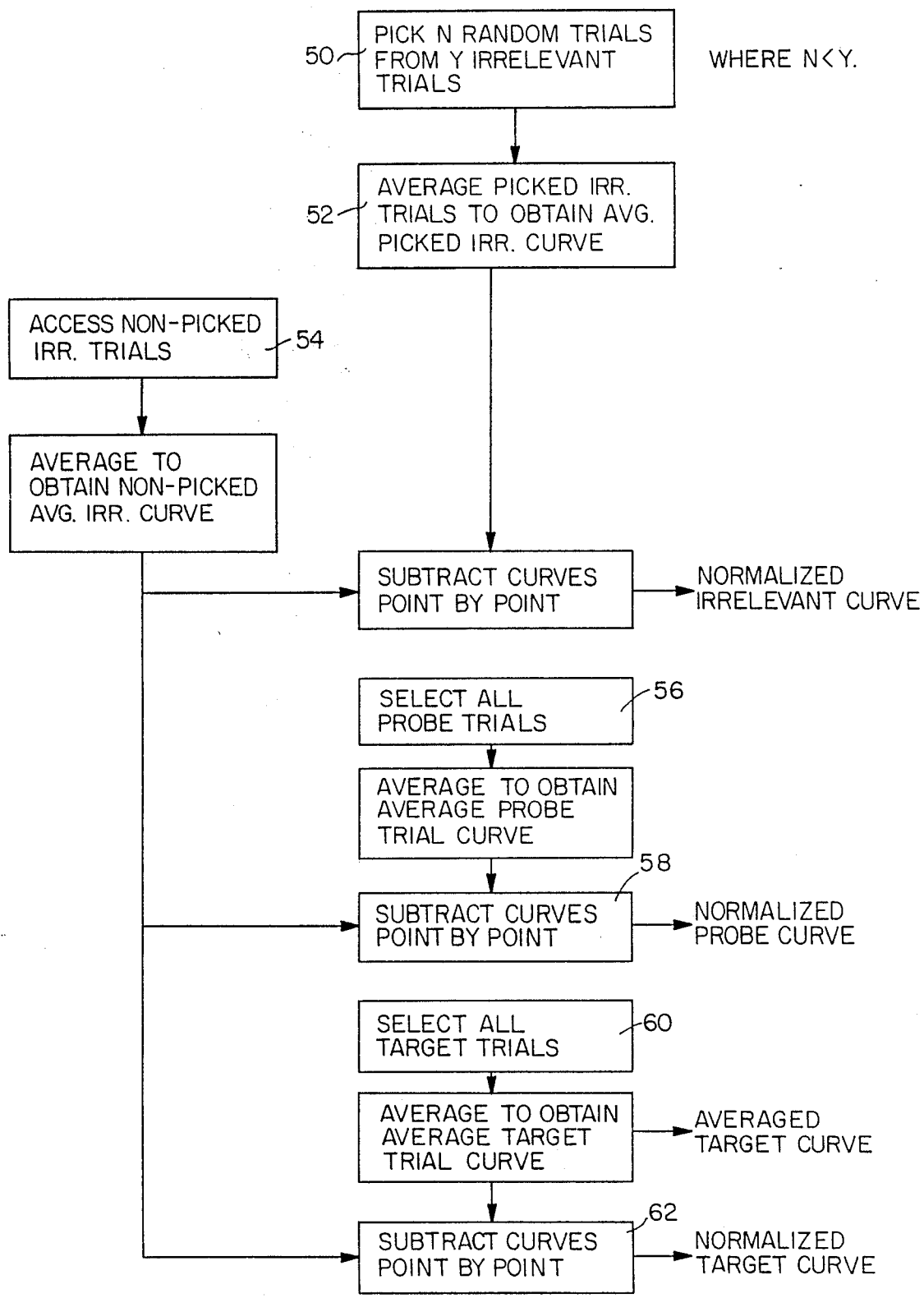
FIG. 4 is a simplified flowchart of a program for creating normalized ERP response curves.

With reference to FIG. 4, preprocessing is required before the actual analysis of the recorded P300's can occur. As shown in FIG. 4, the first step indicated at box 50 requires that a subset of the Irrelevant trials be averaged for subsequent comparison purposes. Thus a randomly chosen subset N of the Irrelevant trials is selected from the Y Irrelevant trials actually run. Assuming that the Y in this case is equal to 96, the system picks twenty-four trials randomly from all of the Irrelevant trials. Then, as shown at 52, the "Picked" Irrelevant trials are averaged on a point by point basis to obtain an overall average Picked Irrelevant curve. The average Picked Irrelevant curve provides a normalized Irrelevant curve as follows. All of the non-picked Irrelevant trials are selected (box 54) and are averaged in the same manner as aforestated to obtain a non-picked average Irrelevant curve. The non-picked average Irrelevant curve is then subtracted from the Picked Irrelevant curve to provide a Normalized Irrelevant curve. This method of normalization eliminates any generalized response from stimuli and determines whether there is a significant difference between the averaged Irrelevant curves which would indicate an unexplained variance and would call the test into question. Under normal circumstances, the Normalized Irrelevant curve should be close to zero, whereas the non-picked Irrelevant curve will indicate the generalized response of the subject to an Irrelevant stimulus.

The averaged non-picked Irrelevant curve is also employed to normalize the P300 curves achieved as the result of the Probe and Target trials. Thus, as shown at Boxes 56 and 60, all Probe trials and Target trials are selected from memory; averaged to obtain Probe trial and Target trial average curves and then subtracted, as shown at Boxes 58 and 62, on a point by point basis, from the averaged non-picked Irrelevant curve. The results are then stored as the Normalized Probe and Normalized Target curves respectively. As aforestated, the Normalized Probe curve is indicative of the P300 component of a subject's ERP in response to Probe stimuli and the Normalized Target curve is the averaged P300 component of the subject's ERP in response to Target stimuli. It should be noted that for each repetition of this routine, the random choice of the Irrelevant trials changes and the normalized curves are altered somewhat. Subsequent analysis of the variations, as above stated, provides the user with an enhanced statistical confidence factor that aberrations have not negated the efficacy of the analysis.

Figure 5:
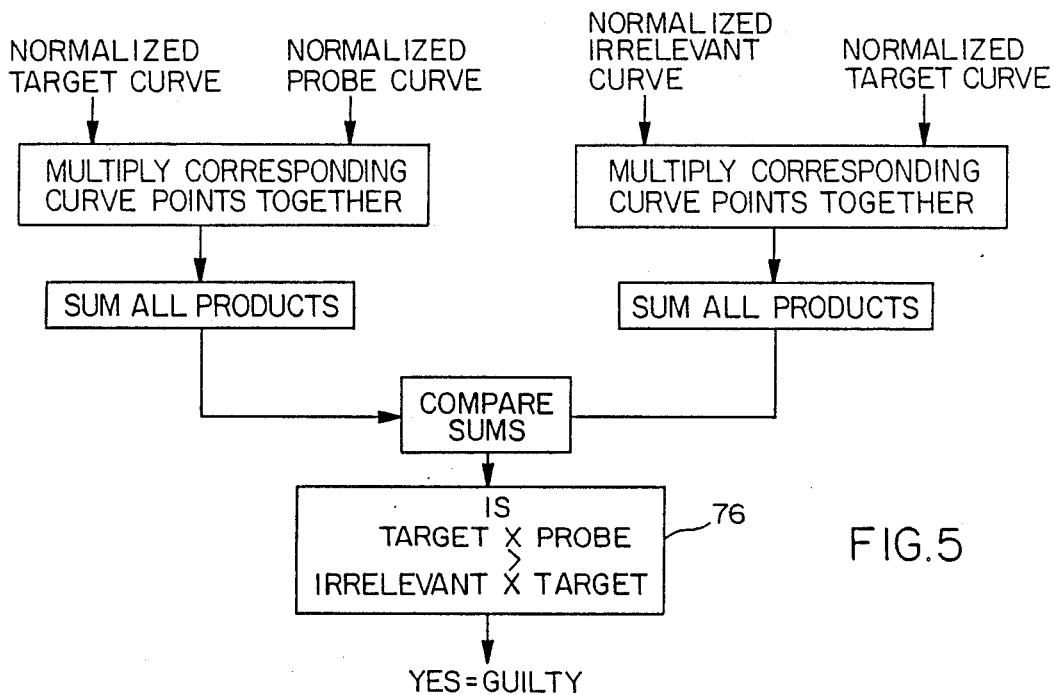
FIG. 5 is a simplified flowchart of a program which determines from normalized P300 curves the guilt of a subject.

Turning now to FIG. 5, a simplified flow diagram showing the "guilty" test is illustrated. The Normalized Target and Probe curves are accessed and their corresponding curve points are each multiplied together (Box 70). Subsequently, all products resulting from the multiplication are summed to provide a single number. The same function occurs at Box 72 with respect to the Normalized Irrelevant curve points and the Normalized Target curve points. The sums are then compared to determine whether the Target x Probe summed products are greater than the Irrelevant x Target summed products. The multiplication step provides an enhancement of any differences between the products.

If the Normalized Probe curve evidences a substantial P300 component waveform, its multiplication by the Normalized Target curve—which also evidences a substantial P300 component—should result in a sum which is significantly larger than the value associated with the Irrelevant stimuli. This indicates that the subject being interrogated responded to the Probe stimuli with a substantial P300 component indicating that the subject was familiar with the incriminating evidence. On the other hand, the product of the Normalized Picked Irrelevant and Target curves should be smaller because the P300 components of the Normalized Irrelevant are expected to be smaller. If, however, the Normalized Probe curve and the Normalized Irrelevant curves are similar in shape, their respective multiplication by the Normalized Target curve will not change that fact and a potential innocent finding will be indicated. Thus, as shown at Box 76, if the product of the Target times the Probe is greater than the product of the Irrelevant times the Target, there is an indication of special knowledge or "guilty knowledge", which in the appropriate circumstances can be an indication of guilt. If on subsequent tries, the condition shown in Box 76 is continuously fulfilled, then the statistical confidence of the guilt indication is increased.

Figure 6:
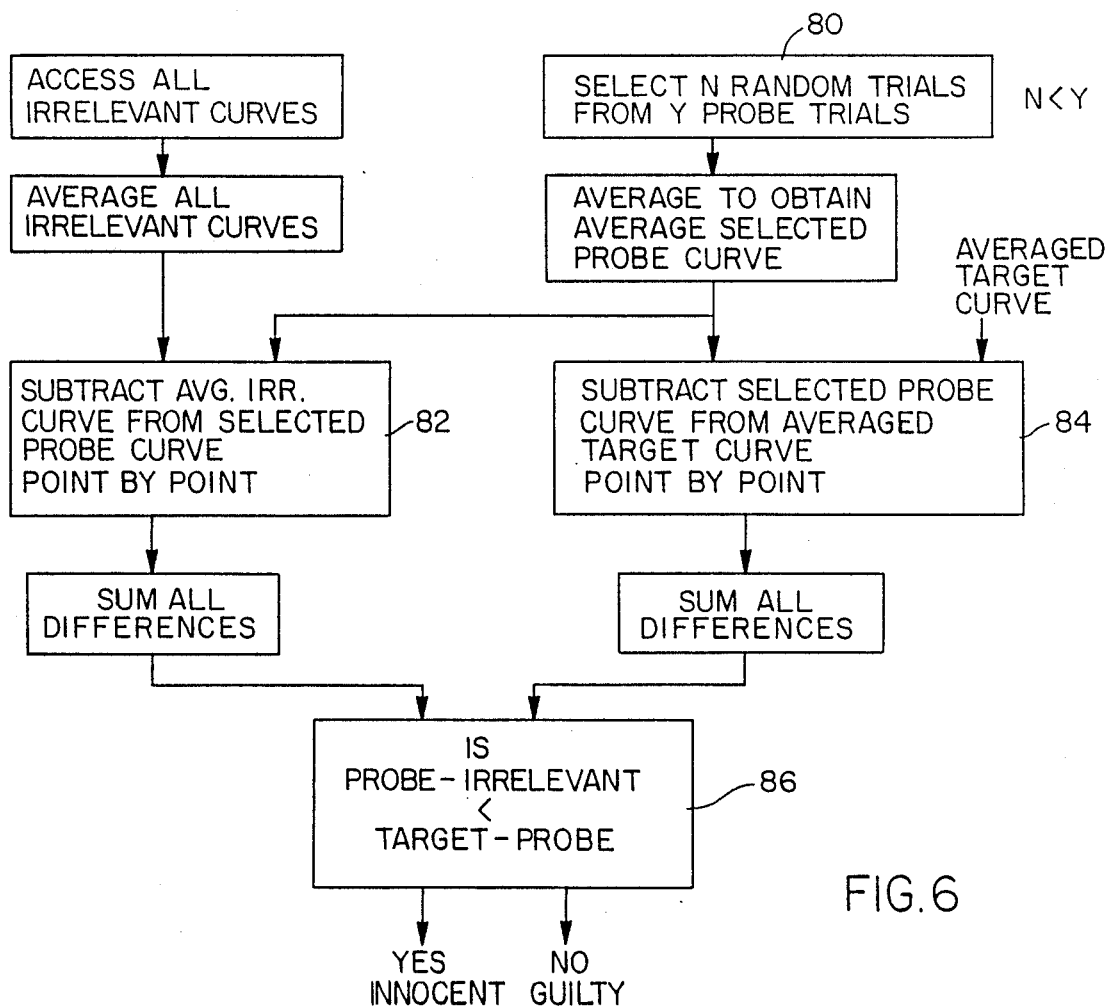
FIG. 6 is a simplified flowchart of a program which determines from averaged P300 curves the innocence of a subject.

Turning now to FIG. 6, a flow chart which enables an independent innocent test to be performed is shown. As shown at Box 80, a subset of the Probe trials is selected and then averaged to obtain a Selected Probe curve. (Remember that the Probe curve evidences a substantial P300 component if the subject recognizes the Probe stimuli as relevant.) The Selected Probe curve then has subtracted from it the Averaged Irrelevant curve as shown at Box 82. Additionally, the Probe curve is subtracted from the averaged Target curve on a point by point basis as shown in Box 84. The respective curve point differences are then summed to provide a number indicating the overall differences of the selected Probe curve from the averaged Irrelevant curve and of the Selected Probe curve from the averaged Target curve. The sums are then compared, and if the Probe less Irrelevant difference is smaller than the Target less Probe difference, then an innocent indication is provided.

The logical basis of this test is as follows: If the party being questioned is innocent, the Probe and Irrelevant ERP responses will be similar and will lack a P300 component. On the other hand, the Target responses will indicate substantial P300's. Thus, for an innocent party, it would be expected that the subtraction of the Probe curve from the Target curve will result in a larger number than the Irrelevant curve subtracted from the Probe curve. If, however, the Probe responses from the selected Probe trials evidence high P300 components, then the condition indicated in Box 86 will not occur, and there will be an additional indication of guilt. The guilt indication occurring from the test shown in the subroutine of FIG. 6 is not as powerful as that shown in FIG. 5 due to the fact that the multiplication which occurs in the subroutine of FIG. 5 enhances the differences in the data and provides a more statistically reliable indication of guilt.

It should be noted that the procedures shown in FIGS. 4, 5 and 6 are repeated many times (e.g. 1000) so as to statistically determine whether there are any random differences which would call the test into question. The repetition of the procedures provides substantial confidence of the efficacy of the findings.

EXPERIMENTAL

Four subjects were tested who acknowledged having committed a particular crime or other similar socially undesirable act. Each subject was tested in two conditions: "guilty" and "innocent". Stimuli of 3 different categories, Probe, Irrelevant, and Target, were presented one by one on a CRT under computer control. Prior to stimulus presentations of the CRT, the subjects were presented with a list of all of the stimuli on paper, without any indications of stimulus categories. Subjects were informed that those stimuli would appear one at a time at the top of the CRT screen. Before the one-by-one stimulus presentations began, the target stimuli appeared at the bottom of the CRT screen and remained there. Subjects were instructed to count all occurrences of these target stimuli at the top of the screen during the upcoming one-by-one stimulus presentation. The types of stimuli and predicted ERP responses are outlined in FIG. 7. In the "guilty" condition, Probe stimuli were words or phrases directly relevant to the crime, and unknown except to the guilty individual. Irrelevant stimuli were similar, but unrelated to the crime. Subjects were not instructed to respond to these types of stimuli. Target stimuli were similar stimuli that subjects were instructed to count. Targets differed from probes and irrelevants only in that the subject had been instructed to count them when they were flashed at the top of the CRT, and a list of the Target stimuli appeared at the bottom of the CRT continuously throughout the session as a memory aid.

Examples of the 3 types of stimuli:
Crime:
  rob Fort Knox
  enter through north tunnel
  disguised as a phone repairman
Stimuli:
  Probe: north tunnel; phone repairman uniform
  Irrelevant: south tunnel; appliance repairman uniform
  Target: east tunnel; electrical repairman uniform subject instructed to count target stimuli In the "innocent" condition, each subject was presented with the stimuli relevant to another subject's crime, which was unknown to the subject being tested. Therefore, the Probe and Irrelevant stimuli were indistinguishable.

It was predicted (1) that the Target stimuli, being rare and task-relevant, would elicit a P300; (2) that the Irrelevant stimuli, being frequent and Irrelevant, would not elicit a P300; and (3) that the Probe stimuli would elicit a P300 only when the subject had "guilty knowledge", and not when the subject was "innocent".

ERP Recording:

Each subject was repeatedly presented with 36 unique stimuli consisting of short phrases on a CRT under computer control. Stimulus duration was 300 msec. Inter-stimulus interval was 1500 msec. Six unique stimuli were Probes, 6 were Targets, and 24 were Irrelevants. Each stimulus was presented a total of 4 times, for an overall total of 144 trials. Order was randomized within each group of 36. EEG was recorded from Fz, Cz, and Pz electrodes. Digitizing rate was 50 Hz.

FIG. 8 displays the average ERP waveforms at Pz for each subject in the "innocent" and "guilty" conditions. The difference between "innocent" and 'guilty' waveforms is readily apparent. In every case, the Irrelevant stimuli elicited little or no P300 and the Target stimuli elicited a large P300. In the "innocent" condition, the Probe (crime-relevant) stimuli elicited little or no P300. In the "guilty" condition, the Probe stimuli elicited a large P300.

Data Analysis

To evaluate the significance of the apparent differences in FIG. 8, the 3 trial types were compared using the iterative sampling procedure heretofore described. The procedures were used to test 2 null hypotheses, a "guilty test" and an "innocent test", for each subject in each condition. (Here "guilty" is used to mean "having crime-relevant knowledge" and "innocent" means "lacking in crime-relevant knowledge".)

I. Guilty Test

The guilty test estimated the probability that the deviation of the Probe trials from the Irrelevant trials in the direction of the Target trials took place by chance. The "guilty" null hypothesis is that Probes do not deviate from Irrelevants in the direction of Targets (any more than randomly chosen subsets of the Irrelevants do). If the "guilty" null hypothesis is rejected, then it is probable that the subject recognizes the Probe (crime-relevant) stimuli as a separate category different from the Irrelevant stimuli, and a "guilty" determination is reached.

To test this hypothesis, 1000 subsets of 24 Irrelevant trials were chosen; their average was compared with that of the Probes; and a count was tallied of the number of times that the Probes differed from the remaining irrelevants in the direction of the Targets more than the randomly chosen subset of the Irrelevants did. The percentage of iterations of the procedure in which this result is found provides a statistical confidence, on an individual subject level, for the "guilty" determination.

II. Innocent Test

If the guilty test fails to reject the null hypothesis, there is no significant indication that the individual is "guilty", but there is also no significant indication that he is "innocent". For this a different null hypothesis needs to be rejected: that the Probe trials are different from the Irrelevants. To test this 1000 subjects of 20 Probe trials were randomly picked, and compared with the Target and Irrelevant averages. If the magnitude of the Picked Probe P300's were consistently closer to the Irrelevant average magnitude than to that of the Targets, then this null hypothesis could be rejected, and an "innocent" determination could be made. As a measure of P300 amplitude the total area under the curve between 280 and 800 msec. post-stimulus at all electrode sites was used.

| Sub- | Determinations and Statistical Confidence | | | |
|---|---|---|---|---|
| | Guilty Condition | | Innocent Condition | |
| ject | Determination | Confidence | Determination | Confidence |
| 1 | Guilty | .999 | Innocent | .999 |
| 2 | Guilty | .999 | Innocent | .985 |
| 3 | Guilty | .999 | Innocent | .999 |
| 4 | Guilty | .999 | Innocent | .999 |
| | Average Confidence | .999 | Average Confidence | .996 |
| | Percent Correct | 100% | Percent Correct | 100% |

The above table displays the determinations and statistical confidence for the 8 cases. The invention was 100% accurate in detecting both "guilty knowledge" and lack of same. Statistical confidence was at least 99.9% in 7 cases, and 98.5% in one case.

We claim:

1. A method for determining if a subject is concealing information concerning an event which comprises:
   exposing the subject to both relevant and irrelevant multiple information stimuli concerning an event;
   monitoring the subject's EEF outputs in response to said stimuli;
   segregating the subject's EEF outputs generated in response to said relevant and irrelevant stimuli; and
   determining any difference between the segregated EEF outputs.

2. A method according to claim 1 wherein the information stimuli includes target stimuli and instructing the subject to perform a task in response to the target stimuli.

3. The method according to claim 2 wherein the EEF output in response to the target stimuli provides a P300 component standard for the subject.

4. A method according to claim 1 wherein said outputs are event related potentials (ERP).

5. A method according to claim 4 wherein the ERP contain P300 components.

6. The method according to claim 4 wherein the stimuli further comprise target stimuli.

7. A method for determining if a subject is concealing information concerning an event which comprises:
   exposing the subject to probe, irrelevant, and target stimuli concerning an event;
   monitoring the subject's ERP responses to said exposure;
   segregating the ERP responses according to stimuli type;
   multiplying together the responses from the target and probe stimuli to obtain a first datum;
   multiplying together the responses from the target and irrelevant stimuli to obtain a second datum; and
   determining any difference between said datum.

8. A method according to claim 7 wherein the ERP contain P300 components.

9. A method for determining if a subject is concealing information concerning an event which comprises:
   exposing the subject to probe, irrelevant, and target stimuli;
   monitoring the subject's ERP response to said exposure;
   segregating the responses according to stimulus type;
   computing a correlation between the target response and the probe response to obtain a first datum;
   computing a correlation between the irrelevant response and the probe response to obtain a second datum; and
   determining any difference between said data.

10. A method according to claim 9 wherein stimuli of each type are average.

11. A method according to claim 9 wherein the ERP responses contain P300 components.

12. A method for determining if a subject is concealing information concerning an event which comprises:
    exposing the subject to probe, irrelevant, and target stimuli;
    monitoring the subject's ERP responses to said exposure;
    segregating the responses according to stimulus type;
    averaging the responses of each type;
    computing a correlation between the average target response and the average probe response to obtain a first datum;
    computing a correlation between the average irrelevant response and the average probe response to obtain a second datum; and
    determining any differences between said data.

13. A method according to claim 12 wherein the ERP responses contain P300 components.

14. A method for determining if a subject is concealing information concerning an event which comprises:
    exposing the subject to probe, irrelevant, and target stimuli;
    monitoring the subject's ERP response to said exposure;
    segregating the responses according to stimulus type;
    comparing the amplitude of the P300 component of the ERPs for the different stimulus types.

15. A method according to claim 14 including averaging the ERPs for each stimulus type prior to comparison of P300 component amplitudes.

16. A method for determining if a subject is concealing information concerning an event which comprises:
    exposing the subject to probe, irrelevant, and target stimuli;
    monitoring the subject's ERP responses to said exposure;
    segregating the responses according to stimulus type;
    comparing the target response and the probe response to obtain a first datum;
    comparing the irrelevant response and the probe response to obtain a second datum; and
    determining any differences between said data.

* * * * *

UNITED STATES PATENT AND TRADEMARK OFFICE
CERTIFICATE OF CORRECTION

PATENT NO. : 4,941,477

DATED : July 17th 1990

INVENTOR(S) : Lawrence A. Farwell and Emanuel Donchin

It is certified that error appears in the above-identified patent and that said Letters Patent is hereby corrected as shown below:

On the cover sheet, line 73 should read:

-- Inventor: Lawrence A. Farwell and Emanuel Donchin, both of Urbana, Ill. --

On the cover sheet, line 73 should read:

-- Assignee: University of Illinois Board Of Trustees, Urbana, Ill. --

Signed and Sealed this

Eighth Day of October, 1991

*Attest:*

HARRY F. MANBECK, JR.

*Attesting Officer*   *Commissioner of Patents and Trademarks*